US008951256B2

(12) United States Patent
Burroughs (10) Patent No.: US 8,951,256 B2
(45) Date of Patent: Feb. 10, 2015

(54) SYSTEM AND METHOD FOR ORIENTING ORTHOPEDIC IMPLANTS

(75) Inventor: Brian R. Burroughs, Worcester, MA (US)

(73) Assignee: University of Massachusetts, Boston, MA (US)

( * ) Notice: Subject to any disclaimer, the term of this patent is extended or adjusted under 35 U.S.C. 154(b) by 267 days.

(21) Appl. No.: 13/367,223

(22) Filed: Feb. 6, 2012

(65) Prior Publication Data

US 2012/0136402 A1      May 31, 2012

Related U.S. Application Data

(63) Continuation-in-part of application No. 13/303,728, filed on Nov. 23, 2011.

(60) Provisional application No. 61/458,396, filed on Nov. 23, 2010.

(51) Int. Cl.
*A61B 17/56*     (2006.01)
*A61B 19/00*     (2006.01)
*A61B 6/04*      (2006.01)
*A61F 2/46*      (2006.01)

(52) U.S. Cl.
CPC .......... *A61B 19/5244* (2013.01); *A61B 6/0421* (2013.01); *A61B 19/56* (2013.01); *A61B 2019/5248* (2013.01); *A61B 2019/5272* (2013.01); *A61F 2/4609* (2013.01); *A61F 2002/4687* (2013.01)
USPC ....................................... 606/86 R

(58) Field of Classification Search
CPC ........ A61B 5/103; A61B 5/05; A61B 6/0421; A61B 19/56; A61B 2019/5272; A61B 2019/5248
USPC ........... 606/86 R, 91, 130; 600/407, 424, 587
See application file for complete search history.

(56) References Cited

U.S. PATENT DOCUMENTS 6,122,538 A * 9/2000 Sliwa et al. .................... 600/407
2005/0251026 A1 * 11/2005 Stone ............................ 600/424

* cited by examiner

*Primary Examiner* — Christopher Beccia
(74) *Attorney, Agent, or Firm* — Milstein Zhang & Wu LLC; Joseph B. Milstein (57) ABSTRACT

A surgical guidance system for properly orienting a surgical instrument, such as an acetabular cup inserter, within a patient relative to a plurality of anatomical reference points includes a support device for retaining the patient, a reference sensor fixedly coupled to the support device and a tool sensor removably coupled to the instrument. The support device includes a plurality of abutment pads that directly contact the plurality of anatomical reference points. A processor is electrically connected to the reference and tool sensors and is programmed to collect spatial orientation data compiled from each sensor. Using the spatial orientation data, the processor determines in real-time the actual orientation of the surgical instrument relative to the anatomical reference points. An indicator is electrically connected to the processor and provides a feedback signal that assists the surgeon in properly orienting the instrument relative to a user-defined acceptable range.

15 Claims, 5 Drawing Sheets

SYSTEM AND METHOD FOR ORIENTING ORTHOPEDIC IMPLANTS

CROSS-REFERENCE TO RELATED APPLICATIONS

The present application is a continuation-in-part of U.S. patent application Ser. No. 13/303,728, which was filed on Nov. 23, 2011 in the name of Brian R. Burroughs, which in turn claims the benefit of U.S. Provisional Patent Application Ser. No. 61/458,396, which was filed on Nov. 23, 2010 in the name of Brian R. Burroughs, both of the aforementioned disclosures being incorporated herein by reference.

FIELD OF THE INVENTION

The present invention relates generally to systems and methods for surgically implanting prosthetic components and more particularly to surgical guidance systems for use in properly orienting orthopedic implants in a patient.

BACKGROUND OF THE INVENTION

The acetabulofemoral joint, commonly referred to simply as the hip joint, is a ball-and-socket joint that is formed through articulation of the rounded, ball-shaped head of the femur (commonly referred to in the art as the femoral head) within the cup-like hip socket, or acetabulum, that is formed in the pelvic bone. Functional limitations and discomfort in the hip joint can result from a myriad of different factors, such as arthritic conditions, degeneration of the femoral and pelvic bones and/or physical trauma. In extreme circumstances, regression of the hip joint ultimately necessitates the implantation of prosthetic components to restore useful functionality of the hip joint.

For instance, total hip replacement surgery is an increasingly common surgical procedure that involves replacement of the femoral head and the acetabulum with corresponding implantable prosthetic components. In the first step of the surgical process, the patient is disposed on a surgical table in either the supine position (i.e., lying face up with the anterior aspect of the pelvis disposed directly upward) or the lateral decubitus position (i.e., with the hip joint to be repaired facing directly upward). The patient is then firmly retained in place using a hip positioning device that is fixedly secured to the surgical table. One type of hip positioning device which is well known in the art to position the patient in the lateral decubitus position includes a pair of opposing support members that firmly bear against the anterior and posterior aspect of the pelvis. Together, the support members serve to hold the pelvis stable during the hip replacement procedure.

Upon incising the patient, the ligaments and muscle in the hip joint region are separated to permit access to the hip joint. The native femoral head is then severed from the remainder of the femur by cutting through the femoral neck using an appropriate surgical instrument, such as a saw.

With the native femoral head removed therefrom, the acetabulum is then reconstructed. Specifically, the hip socket is first reamed to remove articular cartilage and shape the pelvic bone in its desired configuration (i.e., as a smoothed, hemispherical, cup-like socket). After completion of the reaming process, a prosthetic, cup-like, acetabular component (also referred to in the art simply as an acetabular cup) is removably mounted onto the proximal end of an elongated, rod-shaped implantation instrument that is commonly referred to in the art as an inserter. Holding the distal end of the inserter, the acetabular component is aligned within the reamed portion of the pelvis.

The acetabular component is often fittingly retained in place, or impacted, within the reamed acetabulum by forceably striking the distal end of the implantation with a mallet or other similar instrument. Various means are used to additionally secure the acetabular component within the hip socket and include, inter alia, (i) applying an adhesive between the acetabular component and the pelvic bone, (ii) driving fastening elements (e.g., screws) through the acetabular component and into the pelvic bone and (iii) roughening the exterior surface of the acetabular component to promote frictional engagement with the pelvic bone.

Once implantation of the acetabular component is completed, the proximal end of the femur is hollowed out so as to define a canal that is dimensioned to fittingly receive the elongated metal stem for the femoral component, the stem being preferably retained therein using any combination of adhesives, fastening elements and/or frictional engagement. With the stem of the femoral component retained within the femur, the prosthetic femoral head (typically constructed as a metal ball) is secured onto the free end of the stem. Once implantation of the femoral and acetabular prosthetics has been completed, the artificial femoral head is disposed within the artificial acetabulum, thereby completing reconstruction of the acetabulofemoral joint.

The success rate associated with total hip replacement surgery has been found to be largely dependent upon a number of relevant factors. In particular, it has been found that proper orientation of the implanted acetabular component within the reamed pelvic region is critical to the overall success of the surgery. Improper orientation of the acetabular component can lead to, among other things, component impingement as well as dislocation of the hip joint, which is highly undesirable. Accordingly, it is to be understood that implanting the acetabular component in the proper orientation relative to the pelvis is of paramount importance.

Figure 1:
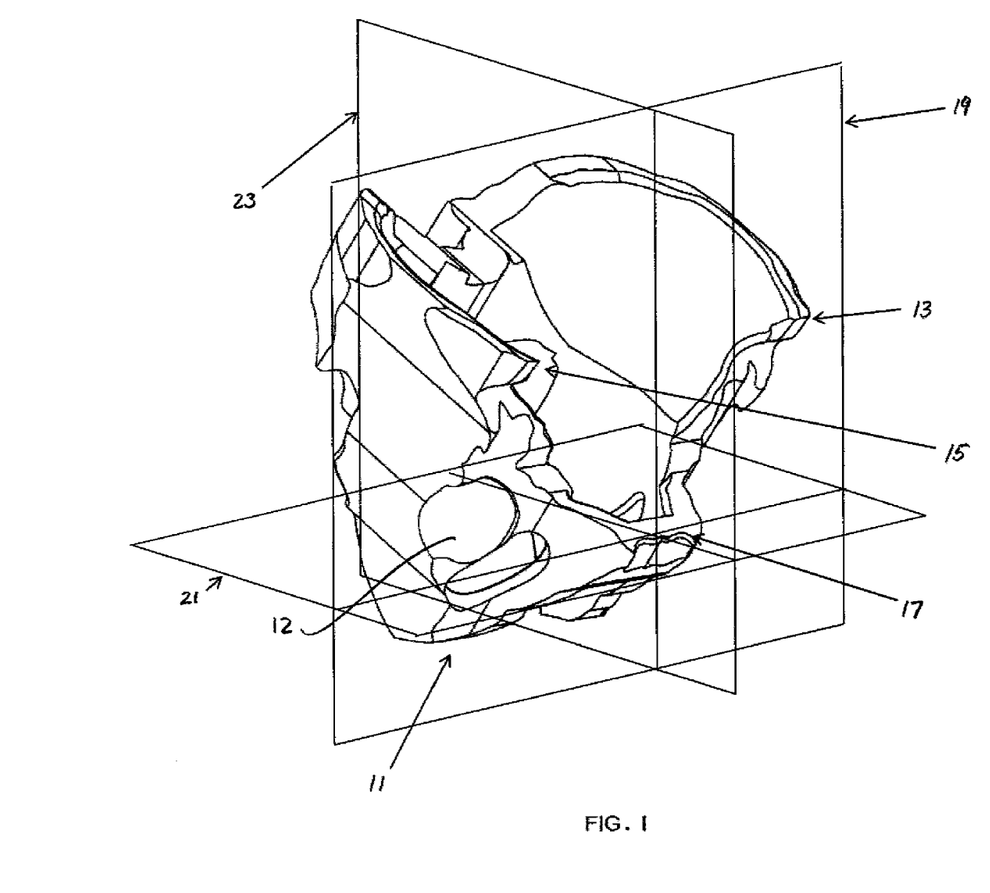
FIG. 1 is a front perspective view of a normal human pelvis, the pelvis being shown with the anterior pelvic, transverse and sagittal reference planes defined in relation thereto.

Traditionally, proper orientation of the acetabular component is accomplished by the surgeon by identifying certain anatomical landmarks on the pelvis and, in turn, visually estimating the proper angle of orientation relative thereto. Referring now to FIG. 1, there is shown a front perspective view of a normal human pelvis 11 that is oriented such that the right acetabulum 12 is readily identifiable. As can be seen, pelvis 11 includes three imaginary orthogonal reference planes that are defined using specified anatomical landmarks. Specifically, the left anterior superior iliac spine (ASIS) 13, the right anterior superior iliac spine 15 and the pubic symphysis 17 together define the anterior pelvic plane 19. The anterior pelvic plane 19 extends vertically when the patient is standing upright and runs generally in parallel with the coronal plane of the body (i.e., the vertical plane that separates the body into ventral and dorsal sections). The transverse plane 21 extends horizontally when the patient is standing upright and extends from the left side of pelvis 11 to the right side of pelvis 11. The sagittal plane 23 extends vertically when the patient is standing upright and extends from the front, or anterior, of pelvis 11 to the back, or posterior, of pelvis 11.

Acetabular components are typically constructed from one or more pieces that together create a generally hemispherical cup. As such, it is to be understood that an acetabular component is shaped to define an imaginary center axis that extends through its apex. It is the relationship between the center axis for the acetabular component and the orthogonal planes of pelvis 11 that is used to properly orient the acetabular cup during total hip replacement.

There are two primary angles that are used to properly orient an acetabular component within reamed acetabulum 12, namely, (i) abduction and (ii) anteversion. Abduction of the acetabular component is the angle between transverse plane 21 and the main axis for the acetabular cup as projected onto anterior pelvic plane 19. Anteversion of the acetabular component is the angle between anterior pelvic plane 19 and the main axis for the acetabular cup as projected onto transverse plane 21. Traditionally, the ideal orientation of an acetabular cup within reamed acetabulum 12 is defined as approximately 40-50 degrees of abduction and approximately 15-25 degrees of anteversion.

Visual estimation of the abduction and anteversion angles has been found to be very difficult to assess during total hip replacement since the aforementioned pelvic reference planes are imaginary in nature. In addition, it should be noted that the pelvis is encased in soft tissue and is typically covered with surgical drapes during the procedure, thereby rendering visualization of the pelvic reference planes nearly impossible to achieve. Furthermore, even if the orientation of the pelvis is accurately determined, the ability of the surgeon to visually estimate instrument angles relative thereto is highly subjective and therefore prone to error.

In view of the aforementioned shortcomings associated with using visual estimation means for determining proper orientation of the acetabular cup, mechanical alignment guides have been recently developed for use in connection with hip replacement surgeries. Mechanical alignment guides provide the surgeon with a visual reference of the orientation of the acetabular component relative to the plane of the patient and operating room table. Although well known and widely used in the art, mechanical alignment guides of the type as described above have been found to have the potential to introduce significant error. In particular, the use of mechanical alignment guides requires that the pelvis be positioned properly prior to draping the patient for surgery, which is not always achieved. In addition, mechanical alignment guides fail to account for any intraoperative changes in pelvic orientation.

Accordingly, electronic surgical guidance systems are well known in the art and are used to assist in properly orienting prosthetic components, such as acetabular components, within a patient. Electronic surgical guidance systems allow for a target, or ideal, orientation angle for the acetabular component to be input into a central controller. Using spatial orientation data derived from sensors mounted on the implantation instrument, the controller provides feedback signals to the surgeon that indicate when the acetabular component is disposed at the desired angle of orientation.

For example, in U.S. Patent Application Publication No. 2010/0249796 to J. H. Nycz, which is incorporated herein by reference, there is disclosed a surgical instrument for implanting a prosthetic member. The instrument includes an orientation sensor that detects an initial orientation of the prosthetic member and an implanting orientation of the prosthetic member. The instrument further includes a memory module and an input device that receives a user input to transfer the initial orientation detected by the orientation sensor into the memory module for storage. Furthermore, the instrument includes an orientation feedback device that selectively provides an orientation feedback signal to the user. Moreover, the instrument includes a controller that causes the orientation feedback device to provide the orientation feedback signal when the implanting orientation detected by the orientation sensor is substantially equal to the initial orientation stored in the memory module.

Although well known in the art, surgical guidance systems of the type described above have been found to suffer from a few notable shortcomings.

As a first shortcoming, surgical guidance systems of the type described above are rather complex in their construction and use. As a result, it has been found that the costs associated with such systems are largely prohibitive. In addition, the technical expertise that is required to operate such a system is rather significant and lacks user-intuitiveness and thereby necessitates that the surgeon overcome a considerable learning curve prior to first use, which is highly undesirable.

As a second shortcoming, surgical guidance systems of the type as described above typically require that a reference point, or marker, be electronically identified in the pelvis as part of lengthy preparatory step. Once the reference marker in the pelvis is electronically established, orientation of the instrument is then standardized, or calibrated, relative to the reference marker. As can be appreciated, the aforementioned multi-stepped calibration process has been found to be both time-consuming and labor-intensive in nature, which is highly undesirable.

BRIEF SUMMARY OF THE INVENTION

It is an object of the present invention to provide a new and improved system for properly orienting orthopedic implants within a patient.

It is another object of the present invention to provide a system of the type as described above that provides a surgeon with electronic guidance in properly orienting an acetabular component within the pelvis during implantation.

It is yet another object of the present invention to provide a system of the type as described above into which can be input a target, or ideal, range of orientation of an acetabular component relative to at least one pelvic reference plane.

It is still another object of the present invention to provide a system of the type as described above that provides a feedback signal when the acetabular component falls within the target range of orientation.

It is yet still another object of the present invention to provide a system of the type as described above that does not require standardization, or calibration to a particular orientation, prior to each surgery.

It is another object of the present invention to provide a system of the type as described above that has a limited number of parts, is inexpensive to manufacture and is easy to use.

Accordingly, as a principal feature of the present invention, there is provided a surgical guidance system for use in properly orienting a surgical instrument relative to at least one anatomical reference point on a patient, the patient being retained by a support device that contacts the patient at a particular location relative to the at least one anatomical reference point, the system comprising (a) a reference sensor adapted to be fixedly coupled to the support device, the reference sensor collecting a first set of spatial orientation data relative to a reference axis, (b) a tool sensor adapted to be coupled to the surgical instrument, the tool sensor collecting a second set of spatial orientation data relative to a reference axis, and (c) a processor in electronic communication with the reference sensor and the tool sensor, the processor collecting the first and second sets of spatial orientation data, wherein the processor calculates the actual orientation of the surgical instrument relative to the at least one anatomical reference point using the first and second sets of spatial orientation data.

Various other features and advantages will appear from the description to follow. In the description, reference is made to the accompanying drawings which form a part thereof, and in which is shown by way of illustration, an embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE INVENTION

Referring now to the drawings, there is shown a surgical guidance system constructed according to the teachings of the present invention, the surgical guidance system being identified generally by reference numeral 111. In use, surgical guidance system 111 facilitates proper orientation of a surgical instrument relative to at least one anatomical reference point on a patient, as will be described in detail below.

For simplicity purposes only, surgical guidance system 111 is described herein for use in connection with a full hip replacement procedure. More specifically, system 111 is described in detail herein as being used to facilitate proper orientation of an acetabular component within a pelvis during an implantation process. However, it is to be understood that system 111 is not limited to use assisting in the proper orientation of orthopedic implants, such as acetabular components. Rather, it is envisioned that system 111 could be used in connection with any surgical procedure that requires real-time guidance in maintaining a surgical instrument within a particular range of spatial orientation relative to at least one anatomical reference point on a patient.

Figure 2:
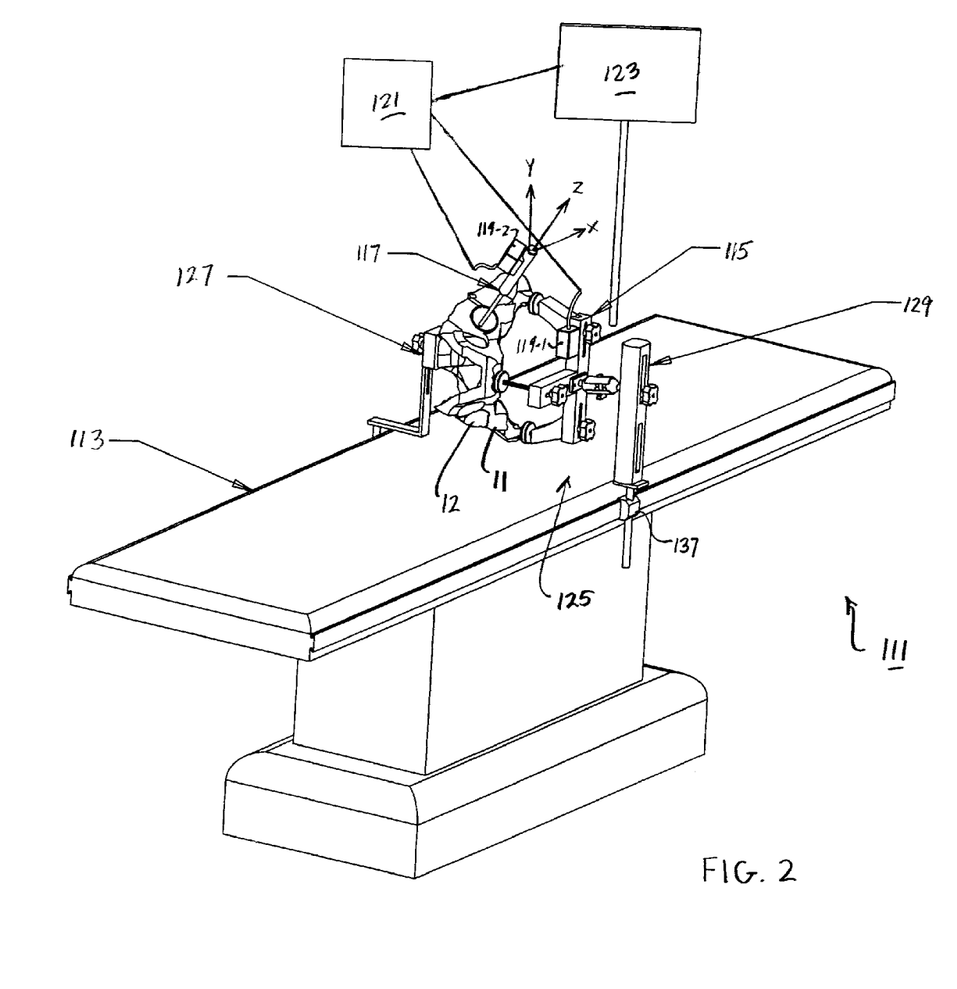
FIG. 2 is a front perspective view of a surgical guidance system constructed according to the teachings of the present invention, the surgical guidance system being shown with a normal human pelvis positioned in the lateral decubitus position therewithin for ease in understanding its use.

As seen most clearly in FIG. 2, surgical guidance system 111 comprises a surgical table 113 adapted to support a patient, a support device 115 fixedly coupled to table 113 for retaining pelvis 11 in a desired position, a surgical instrument 117 for use in implanting a prosthetic component in pelvis 11, a reference sensor 119-1 fixedly coupled to support device 115 for collecting spatial orientation data that can be used to locate at least one anatomical reference point on pelvis 11, a tool sensor 119-2 coupled to instrument 117 for collecting spatial orientation data that can be used to identify the orientation of instrument 117, a processor 121 electrically coupled to sensors 119 for calculating, in real-time, the spatial orientation of instrument 117 relative to the at least one anatomical reference point on pelvis 11, and an indicator 123 in electrical communication with processor 121 for providing a feedback signal that relates to the actual orientation of instrument 117 relative to the at least one anatomical reference point on pelvis 11. For purposes of simplicity, only the pelvis 11 of a patient is shown on table 113 in the present example.

As noted above, support device 115 is fixedly mounted onto table 113 and serves, inter alia, to retain pelvis 11 in the desired lateral decubitus position. Support device 115 is represented herein as comprising an anterior component 125 and a posterior component 127 that are independently secured to table 113. Together, components 125 and 127 apply opposing forces on pelvis 11 and thereby serve as a brace for stabilizing pelvis in a fixed position.

Although support device 115 is represented herein as comprising two separate anterior and posterior components 125 and 127, it is to be understood that support device 115 could be alternatively constructed as a unitary, generally U-shaped component without departing from the spirit of the present invention.

As seen most clearly in FIGS. 2 and 3, anterior component 125 comprises a vertical support beam 129, a generally T-shaped frame 131 pivotally coupled to support beam 129, upper and lower arms 133-1 and 133-2 slidably coupled to frame 131 and a plurality of stability members 135 for locating and applying pressure onto selected bony landmarks on pelvis 11, as will be described further in detail below.

Support beam 129 is an elongated, rigid member that is fixedly secured to table 113 by a clamp 137 or other similar coupling mechanism. As can be seen, support beam 129 is preferably coupled to table 113 in such a manner so as to extend in a generally vertical orientation. An elongated stem 139 is fixedly secured to beam 129 and extends outwardly therefrom in the direction towards posterior component 127. An enlarged ball 141 is formed onto the free end of stem 137 and assists in the pivotal coupling of frame 131 to support beam 129, as will be described further below.

Figure 3:
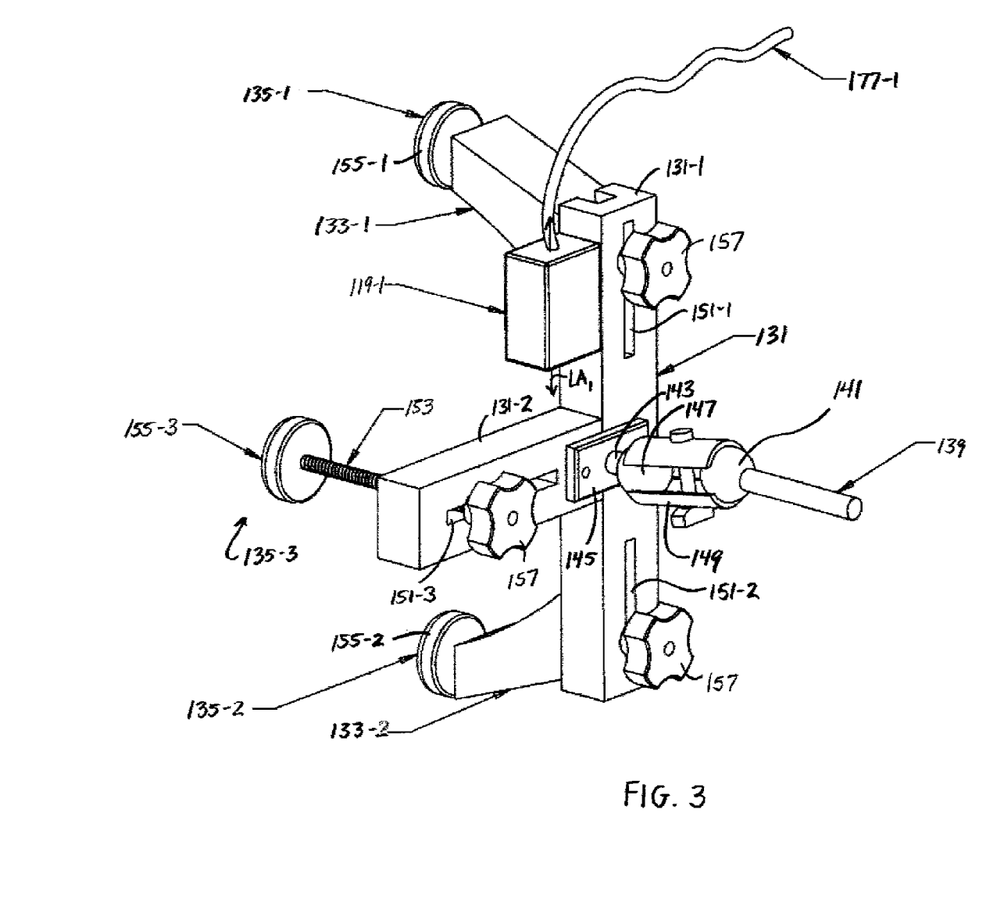
FIG. 3 is a front perspective view of the anterior component of the support device shown in FIG. 1, the support device being shown with the reference sensor fixedly mounted thereon.

As seen most clearly in FIG. 3, T-shaped frame 131 is a rigid, unitary member that includes a vertical portion 131-1 that is generally U-shaped in transverse cross-section and a horizontal portion 131-2 that extends in a generally orthogonal relationship relative to vertical portion 131-1. A shortened stem 143 extends orthogonally out from the anterior side of frame 131 and is secured thereto by a bracket 145. An enlarged ball 147 is formed on the free end of shortened stem 143 and is coupled to ball 141 by a clamp 149 that is generally C-shaped in transverse cross-section.

As can be appreciated, clamp 149 is designed to be tightened in order to securely retain balls 141 and 147 therewithin. Due to its rounded construction, each of balls 141 and 147 is capable of rotation within clamp 149. In this capacity, ball 141, ball 147 and clamp 149 together create a pivotal coupling mechanism that enables frame 131 to pivot freely in all directions relative to beam 129, which is useful to account for any pelvic obliquity.

Upper and lower arms 133-1 and 133-2 are independently slidably coupled to vertical portion 131-1 at opposite ends thereof. Specifically, upper arm 133-1 is secured to frame 131 by a first stability member, or outrigger, 135-1 that extends longitudinally through arm 133-1 and, in turn, transversely through a vertical slot 151-1 formed in the upper region of vertical portion 131-1. Similarly, lower arm 133-2 is secured to frame 131 by a second stability member, or outrigger, 135-2 that extends longitudinally through arm 133-2 and, in turn, transversely through a vertical slot 151-2 formed in the lower region of vertical portion 131-1. Although outriggers 135-1 and 135-2 are represented herein as unitary members that extend through the entirety of arms 133-1 and 133-2, respectively, it is to be understood that each of outriggers 135-1 and 135-2 could be alternatively constructed as a plurality of separate pieces (e.g., with a first piece extending outward from one end of each arm 133 and a second section extending out from the opposite end of each arm 133) without departing from the spirit of the present invention.

In addition, it should be noted that a third stability member 135-3 is provided that extends transversely through a lateral slot 151-3 formed in horizontal portion 131-2. As will be described further in detail below, stability members 135 are designed to align and bear directly against corresponding anatomical landmarks on pelvis 11 and thereby assist in defining pelvic reference planes.

Each stability member 135 preferably includes an elongated, externally threaded rod 153 that is dimensioned to fittingly protrude through its associated slot 151. An enlarged abutment, or stability, pad 155 is fixedly mounted onto one end of each threaded rod 153. In the present embodiment, each pad 155 has a sufficiently cushioned, disc-shaped construction. However, it is to be understood that pads 155 could be alternatively constructed without departing from the spirit of the present invention. For example, pads 153-1 and 153-2, which in the present example bear against left ASIS 13 and right ASIS 15, respectively, could be alternatively provided with a curved profile to conform against the lateral aspect of each ASIS in order to provide additional stability to the pelvis.

In use, pads 155 are designed to bear directly against anatomical landmarks on pelvis 11 that are, in turn, used to define anterior pelvic plane 19. Specifically, in the present example, pad 155-1 is disposed in direct contact against the against left ASIS 13, pad 155-2 is disposed in direct contact against right ASIS 15 and pad 155-3 is disposed in direct contact against pubic symphysis 17. As such, the abutment surface, or free end, of pads 155 together define anterior pelvic plane 19.

It should be noted that threaded rods 153-1 thru 153-3 are preferably equal in length. As a result, pads 155-1 thru 155-3 extend in front of frame 131 a generally fixed (i.e. equal) distance. Therefore, it is to be understood that the plane defined by T-shaped frame 133 lies in parallel with the anterior pelvic plane 19 defined by pads 155 (and, as a consequence, generally orthogonal to transverse plane 21 and sagittal plane 23).

Due to the inclusion of linear slots 151, each threaded rod 153 is designed to travel therewithin in order to accommodate variances in the location of anatomical reference points for different size patients. It should be noted that each pad 155 is limited to linear displacement within the defined reference plane (i.e., anterior pelvic plane 19). In other words, pads 155-1 and 155-2 can be vertically adjusted (i.e., along the medial-lateral path) and pad 155-3 can be horizontally adjusted (i.e., along the proximal-distal path). In addition, it should be noted that pad 155-3 can be axially displaced along rod 153 in a limited fashion (i.e., along the anterior-posterior path) to account for slight variances in the amount of soft tissue covering the bony landmark that pad 155-3 is designated to locate.

An enlarged knob 157 is threadingly mounted onto the free end of each rod 153 and is designed to selectively engage frame 131 to fix the position of each stability member 135 in relation to frame 131.

As seen most clearly in FIG. 3, reference sensor 119-1 is fixedly mounted onto vertical portion 131-1 of frame 131 in a co-planar relationship relative thereto. As will be described further in detail below, reference sensor 119-1 is designed to collect spatial orientation data and, in turn, electrically transmit the data to processor 121. Because the main longitudinal axis $LA_1$ of reference sensor 119-1 lies in parallel with the abutment surfaces of pads 155 and, as a consequence, anterior pelvic plane 19, the spatial orientation data collected by reference sensor 119-1 can be readily used to calculate spatial orientation information for each of the various reference planes for pelvis 11.

Although reference sensor 119-1 is shown herein as mounted directly on frame 131, it should be noted that sensor 119-1 could be alternatively mounted onto other fixed objects in the immediate environment (e.g., beam 129 or table 113) as long as the orientation of the main longitudinal axis $LA_1$ for sensor 119-1 is known relative to anterior pelvic plane 19. If reference sensor 119-1 is alternatively mounted onto beam 129 or table 113, it is to be understood that frame 131 is preferably held fixed in relation to beam 129 (i.e., no longer pivotally displaceable) and therefore would no longer be able to account for any obliquity of the pelvis.

Figure 4:
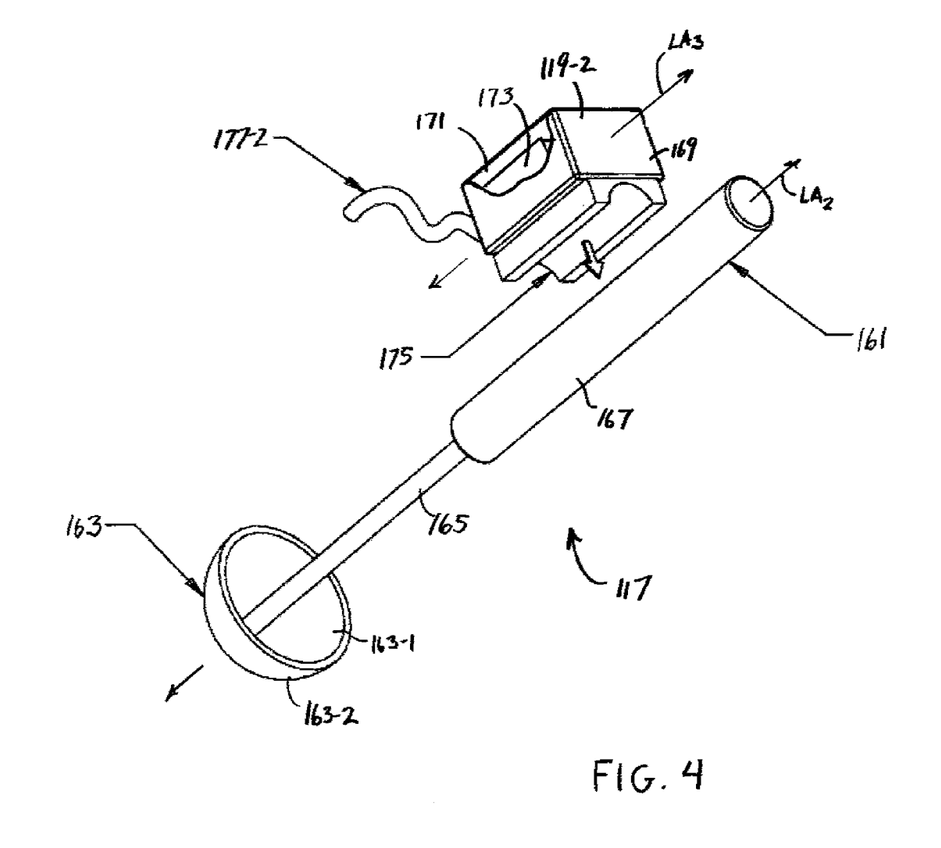
FIG. 4 is a front perspective view of the surgical instrument shown in FIG. 2, the surgical instrument being shown with the tool sensor exploded therefrom, the tool sensor being broken away in part to view its internal circuitry.

Referring now to FIGS. 2 and 4, surgical instrument 117 is represented herein as being in the form of a shell inserter 161 on which is removably mounted an acetabular component 163. As will be described further in detail below, inserter 161 can be used to insert acetabular component 163 in place within a reamed acetabulum in pelvis 11. However, it should be noted that surgical instrument 117 is not limited to tools used to insert acetabular components 163 into the pelvis. Rather, it is to be understood that surgical instrument 117 represents any surgical instrument that would ideally require spatial orientation guidance relative to at least one anatomical reference point on a patient.

Inserter 161 is an elonaged implantation instrument that includes an elongated cylindrical rod 165 on which is coaxially mounted an enlarged handle 167. Together, rod 165 and handle 167 share a common longitudinal axis $LA_2$.

Acetabular component 163 is represented herein as a dome or hemispherically-shaped cup that includes an interior surface 163-1 and an exterior surface 163-2. An internally threaded bore (not shown) is preferably formed into interior surface 163-1 at its approximate center and is dimensioned to receive a complementary threaded element (not shown) formed onto the free end of cylindrical rod 165. In this capacity, it is to be understood that acetabular component 163 can be removably screwed onto inserter 161 in coaxial alignment therewith.

As will be described further below, acetabular component 163 is preferably disposed into proper position within the reamed acetabulum by holding and manipulating handle 167. With acetabular component 163 properly oriented within the reamed acetabulum, the distal end of inserter 161 can be struck with a mallet or other similar instrument to forceably wedge component 163 into place within pelvis 11, outer surface 163-2 being preferably roughened to increase the retentive strength of the impaction.

Tool sensor 119-2 is removably mounted onto handle 167 and is designed to collect spatial orientation data relating to the position of instrument 117, the data being electrically transmitted to processor 121. As seen most clearly in FIG. 4, each sensor 119 preferably includes an outer protective casing 169 that is shaped to define an enclosed interior cavity 171. Casing 169 is generally rectangular in configuration and defines a main longitudinal axis.

A sensor module 173 is disposed within interior cavity 171 and is designed to collect spatial orientation data in relation to its main longitudinal axis (or other similar reference axis). Preferably, sensor module 173 includes both a solid-state, 3-axis accelerometer as well as a 3-axis magnetometer. For example, sensor module 173 may be of the type manufactured and sold by STMicroelectronics of Lexington, Mass. under model number LSM303DLM. However, it is to be understood that sensor module 173 could be provide with additional or alternative spatial orientation detection means, such as a gyroscope, without departing from the spirit of the present invention.

As can be appreciated, the accelerometer and magnetometer for sensor module 173 serve to define coordinate systems that are aligned in relation to the main sensor longitudinal axis (or other similar reference axis). Specifically, the accelerometer measures the direction and magnitude of gravity relative to the reference axis. Similarly, the magnetometer measures the direction and magnitude of the immediate magnetic field relative to the reference axis. Since gravitational and magnetic fields are fixed in space, sensor module 173 can thereby be used to derive spatial orientation data relative to its main reference axis, as will be described further below.

As noted briefly above, reference sensor 119-1 is preferably mounted onto vertical portion 131-1 of frame 131 such that its main longitudinal axis $LA_1$ lies substantially in parallel with pads 155 and, as a consequence, anterior pelvic plane 19. As a result, spatial orientation data collected by reference sensor 119-1 can be readily used by processor 121 to identify the location of each of the various reference planes for pelvis 11 without the need for preliminarily locating and marking anatomical reference points (as well as calibrating instrument sensor 119-2 relative thereto), which is a principal object of the present invention.

Similarly, tool sensor 119-2 is mounted onto handle 167 such that its main longitudinal axis $LA_3$ lies substantially in parallel with the main longitudinal axis $LA_2$ for inserter 161. In this capacity, spatial orientation data collected by reference sensor 119-2 can be used to determine the real-time spatial orientation of instrument 117. Accordingly, processor 121 can utilize the spatial orientation data for instrument 117 (derived from tool sensor 119-2) and the spatial orientation data for the anatomical reference planes (derived from reference sensor 119-1) to guide surgical instrument 117 in the proper orientation relative to pelvis 11, as will be explained further below.

It should be noted that casing 169 for tool sensor 119-1 is preferably provided with a longitudinal recess 175 along its bottom surface that is dimensioned to fittingly receive handle 167. As can be appreciated, the fitted mating relationship between tool sensor 119-1 and handle 167 assures parallel alignment of the longitudinal axis $LA_3$ for sensor 119-1 with the longitudinal axis $LA_2$ of inserter 161, which is highly desirable.

It should also be noted that tool sensor 119-1 is preferably removably mounted onto inserter 161. For example, tool sensor 119-1 may be releasably retained onto handle 167 using straps (or other similar fastening elements) or simply by disposing sensor 119-1 on inserter 161 and manually gripping both elements together. As can be appreciated, the removable mounting of tool sensor 119-1 onto instrument 117 introduces a number of notable advantages including, but not limited to, (i) enabling use of sensor 119-1 on a wide variety of different surgical instruments without the need for preliminary calibration and (ii) permitting proper sterilization of inserter 161 without jeopardizing the electrical integrity of sensor module 173 (with sensor 119-1 being preferably retained within a sterile plastic bag or other similar sterile container during its use).

As noted briefly above, a processor, or central controller, 121 is electrically coupled to sensors 119-1 and 119-2 by wires 177-1 and 177-2, respectively (wires 177 being represented herein, in part, in simplified lined form for ease of illustration). It should be noted that processor 121 need not be connected to sensors 119 by wires 177. Rather, it is to be understood that processor 121 could be electrically coupled to sensors 119 by alternative means (e.g., through wireless communication) without departing from the spirit of the present invention.

In the present example, processor 121 is represented as a stand-alone component that is preferably integrated into a conventional compute device, such as a personal computer. However, it should be noted that processor 121 need not be separate from either sensors 119 or indicator 123. Rather, it is to be understood that processor 121 could be directly integrated into sensor 119-1, sensor 119-2 or indicator 123 without departing from the spirit of the present invention.

As referenced above, each sensor 119 measures the position and magnitude of both gravitational and magnetic field vectors relative to its corresponding reference coordinate system. The measured vector data is then transmitted to processor 121 for analysis. Using a mathematical algorithm programmed thereon, processor 121 is able to calculate the spatial orientation of surgical instrument 117 relative to anterior pelvic plane 19. It is also to be understood that, in the present example, processor 121 can be additionally programmed to calculate the abduction angle and the anteversion angle of acetabular component 163 relative to pelvis 11, which is a principal object of the present invention.

It is important to note that rotation of inserter 117 about its longitudinal axis $LA_2$ cannot be reliably controlled by a surgeon during the implantation process and, in addition, has no bearing in the calculation of either the angle of abduction or anteversion of component 163 relative to pelvis 11. Likewise, the longitudinal location of tool sensor 119-2 along the length of handle 167 cannot be easily maintained. Accordingly, as a principal feature of the present invention, it should be noted that the mathematical algorithm programmed on processor 121 that is used to calculate abduction and anteversion is not affected by any variance in axial rotation or longitudinal displacement of tool sensor 119-2 along handle 167, which is highly desirable.

In particular, spatial orientation data collected from tool sensor 119-2 can be analyzed in view of the anatomical reference planes defined by pelvis 11 (that are, in turn, calculated using spatial orientation data from reference sensor 119-1). As seen in FIG. 2, the relative orientation between tool sensor 119-2 and the pelvic reference planes can be broken down into roll (rotation about the X axis), pitch (rotation about the Y axis) and yaw (rotation about the Z axis). As can be appreciated, rotation of inserter 117 about its longitudinal axis $LA_2$ is equivalent to yaw. Accordingly, since rotation of inserter about its longitudinal axis $LA_2$ is not reliably controlled by the user, the orientation of tool sensor 119-2 is preferably corrected by the algorithm to filter out any rotation about the Z axis. The result is a tool sensor 119-2 that can be used to determine roll and pitch relative to pelvis 11, with roll and pitch being synonymous in this case for anteversion and abduction, respectively.

More specifically, as referenced above, reference sensor 119-1 and tool sensor 119-2 each include a sensor module 173 that comprises a 3-axis accelerometer (not shown) as well as a 3-axis magnetometer (not shown). In use, each accelerometer is designed to measure the direction and magnitude of gravity relative to the local coordinate system of its corresponding sensor 119. Similarly, the magnetometer measures the direction and magnitude of the immediate magnetic field relative to the local coordinate system of its corresponding sensor 119. Since gravitational and magnetic fields are fixed in space, the four aforementioned vectors (namely, reference sensor gravitational vector $A_P$, reference sensor magnetic field vector $M_P$, tool sensor gravitational vector $A_I$, and tool sensor magnetic field vector $M_I$) serve as inputs into the algorithm that in turn can be used to derive spatial orientation data of tool sensor 119-2 relative to the anatomical reference plane.

In the first step of the algorithm, the gravitational and magnetic field vectors associated with each sensor 119 are subject to a series of vector cross products to produce a fixed global orthogonal XYZ coordinate system $Csys_F$. It should be noted that fixed coordinate system $Csys_F$ is fixed in space since each of the gravitational and magnetic field vectors associated with each sensor 119 is similarly fixed in space. In addition, it is to be understood that fixed coordinate system $Csys_F$ is considered herein as the global coordinate system since all sensor angles are measured relative thereto. As such, fixed coordinate system $Csys_F$ is the same for both sensors 119-1 and 119-2. However, the orientation of each sensor 119 can differ relative to fixed coordinate system $Csys_F$, as will be explained further below.

The orientation of each axis of fixed global coordinate system $Csys_{FP}$ is known relative to reference sensor 119-1 and these known orientation axes can be arranged into a 3×3 matrix format (which is referred to herein simply as matrix $G_P$). Similarly, the orientation of each axis of fixed global coordinate system $Csys_{FI}$ is known relative to tool sensor 119-2 and these known orientation axes can be arranged into a 3×3 matrix format (which is referred to herein simply as matrix $G_I$).

In general, the transformation from one orthogonal coordinate system to another orthogonal coordinate system can be described as a series of rotations about each of the individual coordinate system axes for each sensor 119. Therefore, the relationship between fixed global coordinate system $Csys_F$ and the local coordinate system of each sensor 119 can be broken down into three separate rotations about the three individual axes (i.e., axes X, Y, and Z) of fixed global coordinate system $Csys_F$. As referenced briefly above, rotation of each sensor 119 about the X, Y, and Z axes of fixed global coordinate system $Csys_F$ is referred to herein as roll, pitch, and yaw, respectively. Each individual rotation about the X, Y, and Z axes of fixed global coordinate system $Csys_F$ can be described in matrix format. Multiplication of these three individual matrices produces a 3×3 transformation matrix G, which describes the transformation from fixed global coordinate system $Csys_F$ to the local coordinate system of each sensor 119. Each element of matrix G contains a variable expression which can be equated to the numerical value of each element in transformation matrices $G_P$ and $G_I$, respectively. The result is a series of equations which can be used to solve the roll, pitch, and yaw of each sensor 119 relative to fixed global coordinate system $Csys_F$.

It is important to note that the magnitude of each of the three individual rotations (namely, roll, pitch, and yaw) as determined above depends on the assumed order of the individual rotations. For example, consider two different coordinate systems, CS1 and CS2. CS1 can be transformed to CS2 using a finite sequence of roll ($1^{st}$ rotation), pitch ($2^{nd}$ rotation), and yaw ($3^{rd}$ rotation), in that order. However, it is to be understood that the roll, pitch and yaw used to transform CS1 to CS2 will be different if the order of rotation is assumed as pitch ($1^{st}$ rotation), yaw ($2^{nd}$ rotation), and roll ($3^{rd}$ rotation). This variance is due to the fact that, during the transformation of a sequence of rotations about multiple separate axes, the rotation that occurs first in the sequence is unaffected by those rotations that occur to later in the sequence. For example, in a sequence such as roll ($1^{st}$ rotation), pitch ($2^{nd}$ rotation), and yaw ($3^{rd}$ rotation), roll is not affected by pitch and yaw and similarly pitch is not affected by yaw.

This phenomenon can, in turn, be used to eliminate the effect of yaw between sensors 119-1 and 119-2. The objective of the processing algorithm is to define the relative orientation between reference sensor 119-1 and tool sensor 119-2 in terms of two angles, abduction and anteversion, which is synonymous in the art for roll and pitch. Therefore, if roll and pitch are assumed to be the first two rotations in the transformation sequence, the effect of yaw can be eliminated. This allows tool sensor 119-1 to experience any amount of yaw without compromising the calculation of either roll (i.e. abduction) or pitch (i.e. anteversion), which is a principal object of the present invention.

To complete the algorithm of the present invention, the roll and pitch of each sensor 119 relative to fixed global coordinate system $Csys_{FP}$ is determined. The abduction of tool sensor 119-2 relative to reference sensor 119-1 is then calculated by subtracting the roll of reference sensor 119-1 from the roll of tool sensor 119-2. Similarly, anteversion of tool sensor 119-2 relative to reference sensor 119-1 is calculated by subtracting the pitch of reference sensor 119-1 from the pitch of tool sensor 119-2.

The following is an example, using mathematical expressions, of how the algorithm of the present invention is carried out. Specifically, as noted above, reference sensor 119-1 can be used to provide the coordinates of both a gravity vector $A_P$ and a magnetic field vector $M_P$ relative to reference sensor 119-1, wherein:

$$A_P = \begin{bmatrix} x_{AP} \\ y_{AP} \\ z_{AP} \end{bmatrix} \text{ and } M_P = \begin{bmatrix} x_{MP} \\ y_{MP} \\ z_{MP} \end{bmatrix}$$

Similarly, tool sensor 119-2 can be used to provide the coordinates of both a gravity vector $A_I$ and a magnetic field vector $M_I$ relative to tool sensor 119-2, wherein:

$$A_I = \begin{bmatrix} x_{AI} \\ y_{AI} \\ z_{AI} \end{bmatrix} \text{ and } M_I = \begin{bmatrix} x_{MI} \\ y_{MI} \\ z_{MI} \end{bmatrix}$$

Through a series of vector cross-products, a fixed coordinate system $Csys_{FP}$ can be created. As a result, the coordinates of each axis (X, Y, and Z) of fixed coordinate system $Csys_{FP}$ can be determined relative to reference sensor 119-1 in the manner as shown below, wherein:

$$Csys_{FP} = \begin{bmatrix} X_{FP} \\ Y_{FP} \\ Z_{FP} \end{bmatrix}^T = \begin{bmatrix} (A_P \times M_P) \times A_P \\ A_P \times M_P \\ A_P \end{bmatrix}^T = \begin{bmatrix} X_{FPx} & Y_{FPx} & Z_{FPx} \\ X_{FPy} & Y_{FPy} & Z_{FPy} \\ X_{FPz} & Y_{FPz} & Z_{FPz} \end{bmatrix} =$$

-continued $$\begin{bmatrix} (z_{AP}x_{MP} - x_{AP}z_{MP})z_{AP} - \\ (x_{AP}y_{MP} - y_{AP}x_{MP})y_{AP} & y_{AP}z_{MP} - z_{AP}y_{MP} & x_{AP} \\ (x_{AP}y_{MP} - y_{AP}x_{MP})x_{AP} - \\ (y_{AP}z_{MP} - z_{AP}y_{MP})z_{AP} & z_{AP}x_{MP} - x_{AP}z_{MP} & y_{AP} \\ (y_{AP}z_{MP} - z_{AP}y_{MP})y_{AP} - \\ (z_{AP}x_{MP} - x_{AP}z_{MP})x_{AP} & x_{AP}y_{MP} - y_{AP}x_{MP} & z_{AP} \end{bmatrix}$$

Similarly, the coordinates of each axis (X, Y, and Z) of fixed coordinate system $Csys_{FP}$ can be determined relative to tool sensor 119-2 in the manner as shown below, wherein:

$$Csys_{FI} = \begin{bmatrix} X_{FI} \\ Y_{FI} \\ Z_{FI} \end{bmatrix}^T = \begin{bmatrix} (A_I \times M_I) \times A_I \\ A_I \times M_I \\ A_I \end{bmatrix}^T = \begin{vmatrix} X_{Flx} & Y_{Flx} & Z_{Flx} \\ X_{Fly} & Y_{Fly} & Z_{Fly} \\ X_{FLz} & Y_{Flz} & Z_{Flz} \end{vmatrix} =$$

$$\begin{bmatrix} (z_{AI}x_{MI} - x_{AI}z_{MI})z_{AI} - \\ (x_{AI}y_{MI} - y_{AI}x_{MI})y_{AI} & y_{AI}z_{MI} - z_{AI}y_{MI} & x_{AI} \\ (x_{AI}y_{MI} - y_{AI}x_{MI})x_{AI} - \\ (y_{AI}z_{MI} - z_{AI}y_{MI})z_{AI} & z_{AI}x_{MI} - x_{AI}z_{MI} & y_{AI} \\ (y_{AI}z_{MI} - z_{AI}y_{MI})y_{AI} - \\ (z_{AI}x_{MI} - x_{AI}z_{MI})x_{AI} & x_{AI}y_{MI} - y_{AI}x_{MI} & z_{AI} \end{bmatrix}$$

The next step in the spatial processing algorithm is to calculate the roll (i.e., the rotation about X axis) and the pitch (i.e., the rotation about Y axis) of fixed coordinate system $Csys_{FP}$ relative to the local coordinate system of each sensor 119.

Accordingly, a rotation matrix is utilized that transforms the local coordinate system for each sensor 119 into fixed coordinate system $Csys_{FP}$. This rotation matrix is defined using individual transformation matrices G about each of the three individual axes of fixed coordinate system $Csys_{FP}$.

The transformation matrix about the X axis of fixed coordinate system $Csys_{FP}$ (i.e. roll) by an amount γ is as follows:

$$G_{X,\gamma} = \begin{bmatrix} 1 & 0 & 0 \\ 0 & \cos(\gamma) & -\sin(\gamma) \\ 0 & \sin(\gamma) & \cos(\gamma) \end{bmatrix}$$

The transformation matrix about the Y axis of the fixed coordinate system $Csys_{FP}$ (i.e. pitch) by an amount β is as follows:

$$G_{Y,\beta} = \begin{bmatrix} \cos(\beta) & 0 & \sin(\beta) \\ 0 & 1 & 0 \\ -\sin(\beta) & 0 & \cos(\beta) \end{bmatrix}$$

The transformation matrix about the Z axis of the fixed coordinate system $Csys_{FP}$ (i.e. yaw) by an amount α is as follows:

$$G_{Z,\alpha} = \begin{bmatrix} \cos(\alpha) & \sin(\alpha) & 0 \\ -\sin(\alpha) & \cos(\alpha) & 0 \\ 0 & 0 & 1 \end{bmatrix}$$

The three aforementioned individual transformation matrices are then multiplied together to create the general, order-specific, transformation matrix (Matrix $G_{ZYX}$) shown below. It is important to note that, in the present example, the order of rotation is assumed to be roll, pitch, and yaw:

$$G_{ZYX} = G_{Z,\alpha}G_{Y,\beta}G_{X,\gamma} =$$

$$\begin{bmatrix} \cos(\beta)\cos(\alpha) & -\cos(\beta)\sin(\alpha) & \sin(\beta) \\ \sin(\gamma)\sin(\beta)\cos(\alpha) + & -\sin(\gamma)\sin(\beta)\sin(\alpha) + & \\ \cos(\gamma)\sin(\alpha) & \cos(\gamma)\cos(\alpha) & -\sin(\gamma)\cos(\beta) \\ -\cos(\gamma)\sin(\beta)\cos(\alpha) + & \cos(\gamma)\sin(\beta)\sin(\alpha) + & \\ \sin(\gamma)\sin(\alpha) & \sin(\gamma)\cos(\alpha) & \cos(\gamma)\cos(\beta) \end{bmatrix}$$

The expression for each element in the above-identified transformation matrix $G_{ZYX}$ is then equated to the corresponding numerical value in the matrix for fixed coordinate system $Csys_{FP}$. For this example, using elements 1,3 and 2,3 in both fixed coordinate system matrix $Csys_{FP}$ and order-specific transformation matrix $G_{ZYX}$ results in the following set of equations for reference sensor 119-1:

$$Csys_{FP,1,3} = G_{ZYX,1,3} \rightarrow x_{AP} = \sin(\beta_P)$$

$$Csys_{FP,2,3} = G_{ZYX,2,3} \rightarrow y_{AP} = -\sin(\gamma_P)\cos(\beta_P)$$

These two equations can then be solved to determine the pitch and roll for reference sensor 119-1, wherein:

$$\text{pitch}_P = \beta_P = a\sin(x_{AP})$$

$$\text{roll}_P = \gamma_P = a\sin\left(\frac{-y_{AP}}{\cos(a\sin(x_{AP}))}\right)$$

Similarly, the pitch and roll for tool sensor 119-2 can be calculated as:

$$\text{pitch}_I = \beta_I = a\sin(x_{AI})$$

$$\text{roll}_I = \gamma_I = a\sin\left(\frac{-y_{AI}}{\cos(a\sin(x_{AI}))}\right)$$

Having determined the pitch and roll for each sensor 119 in the manner set forth above, the anteversion and abduction of tool sensor 119-2 relative to reference sensor 119-1 can then be determined as:

Anteversion=$\beta_I - \beta_P$

Abduction=$\gamma_I - \gamma_P$

As seen most clearly in FIG. 2, processor 121 is preferably disposed in electrical communication with an indicator 123 that is adapted to provide a real-time visual feedback signal relating to the orientation of instrument 117 relative to defined anatomical reference planes for pelvis 11. In the present example, indicator 123 is represented as a monitor that is disposed in close proximity to the surgeon to allow for greater ease in viewing during the surgical procedure.

It should be noted that indicator 123 is not limited to a monitor to provide a visual feedback signal. Rather, it is to be understood that indicator 123 could be in the form of alternative visual indicators, such as one or an array of light emitting diodes, without departing from the spirit of the present invention.

It should also be noted that indicator 123 need not be separate from the remainder of system 111. Rather, it is to be understood that indicator 123 could be directly integrated into any of the other components of system 111, such as instrument 117, without departing from the spirit of the present invention.

It should further be noted that indicator 123 is not limited to providing a feedback signal that is visual in nature. Rather, it is to be understood that indicator 123 could be provided with additional or alternative sensory feedback means (e.g., an auditory alarm) without departing from the spirit of the present invention.

As will be described further below, a target, or ideal, range of orientation for surgical instrument 117 relative to one or more defined anatomical reference planes can be input into processor 121 to provide surgical guidance during a procedure. In this manner, processor 121 can provide a feedback signal on indicator 123 when instrument 117 falls either inside or outside of the target range.

Figure 5A:
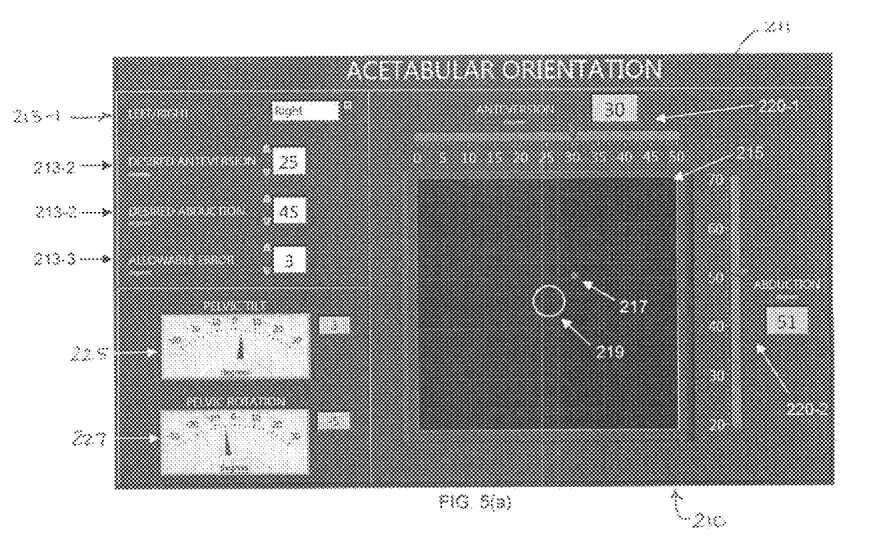
FIGS. 5(a) and 5(b) are sample screen displays provided on the monitor shown in FIG. 2, the sample screen displays being shown at separate stages during the process of orienting the acetabular component within the pelvis.

Specifically, referring now to FIG. 5(a), there is shown a sample screen display 210 of a graphical user interface that is provided on indicator 123 when system 111 is used to implant an acetabular component 163 in pelvis 11, the graphical user interface being identified generally by reference numeral 211. As can be seen, system 111 is designed so that the user is able to input into processor 121 the hip to be replaced (i.e., left or right), the desired, or target, angle of anteversion, the desired, or target, angle of abduction as well as the degree of allowable error, each of said modifiable factors being represented in corresponding user intuitive windows 213-1 thru 213-4, respectively, on graphical interface 211. In the present example, the right hip is set to be replaced, the target angle of anteversion is set at 25 degrees, the target angle of abduction is set at 45 degrees and the amount of allowable error is set at 3 degrees.

Graphical user interface 211 is also designed to include a Cartesian coordinate system, or X-Y, graph 215 that represents the actual angle of anteversion for acetabular component 163 (represented herein as the X axis of the graph) relative to the actual angle of abduction for acetabular component 163 (represented herein as the Y axis of the graph). A dot-shaped cursor 217 is provided on graph 215 that depicts, in real-time, the actual anteversion and abduction angles for acetabular component 163 using the spatial orientation data compiled from sensors 119 and, in turn, processing the data using the mathematical algorithm programmed on processor 121. Accordingly, it is to be understood that as the anteversion and abduction angles for acetabular component 163 vary, the position of cursor 217 moves, or floats, in accordance therewith.

In addition, a ring 219 is provided on graph 215 that depicts the target range of acceptable acetabular orientation. As can be appreciated, the center of ring 219 is defined using the desired angles of anteversion and abduction that are input into processor 121 and, in turn, displayed in windows 213-2 and 213-3, respectively. The diameter of ring 219 is represented as twice the value of the allowable error that is displayed in window 213-4.

Accordingly, it is to be understood that a surgeon can use system 111 in the following manner to ensure proper orientation of an acetabular component 163 in pelvis 11 during the implantation process. Specifically, the patient is positioned in the lateral decubitus position, with pads 155-1 thru 155-3 disposed in direct contact against left ASIS 13, right ASIS 15 and pubic symphysis 17, respectively. As a principal feature of the present invention, spatial orientation data collected from reference sensor 119-1 can be utilized to immediately ascertain the reference planes for pelvis 11 without the need for any (i) complex inspection of the orientation of pelvis 11 or (ii) any preparatory calibration of tool sensor 119-2 relative to one or more reference markings. Rather, once the patient is properly retained by support device 115, system 111 is ready for use, which is highly desirable.

It should be noted that system 111 is not limited to use with the patient disposed in the lateral decubitus position. Rather, it is to be understood that 111 could be utilized with the patient disposed in alternative positions without departing from the spirit of the present invention. For example, system 111 could be implemented with the patient retained by support device 115 in the supine position (i.e., with the anterior aspect of pelvis 11 facing directly upward). As can be appreciated, when system 111 is utilized to perform hip replacement on a patient disposed in the supine position, pads 155 still bear against the anatomical landmarks on patient and therefore define the various pelvic reference planes. However, it should be noted that disposing the patient in the supine position requires that support device 115 be alternatively coupled to table 113 to enable each of pads 155 to bear against the upwardly facing anatomical landmarks. For instance, frame 131 could be held firmly in place against the anterior aspect of the patient using a strap that wraps around the posterior aspect of the patient. Otherwise, a horizontal beam could be attached to vertical beam 129, thereby creating a unitary structure with an L-shaped configuration. Stem 139 would then protrude directly downward from the horizontal beam so that pads 155 are able to abut against the upward facing pelvic landmarks.

After the acetabulum has been properly prepared for implantation, the surgeon grasps handle 167 and manipulates inserter 161 so that acetabular component 163 aligns within the prepared acetabulum. With the target orientation information input into processor 121 (and displayed in windows 213), the user relies upon graph 215 on graphical user interface 211 to properly orientate component 163, with linear anteversion and abduction scales 220-1 and 220-2, respectively, being provided along the periphery of graph 215 to facilitate in the guiding process.

Figure 5B:
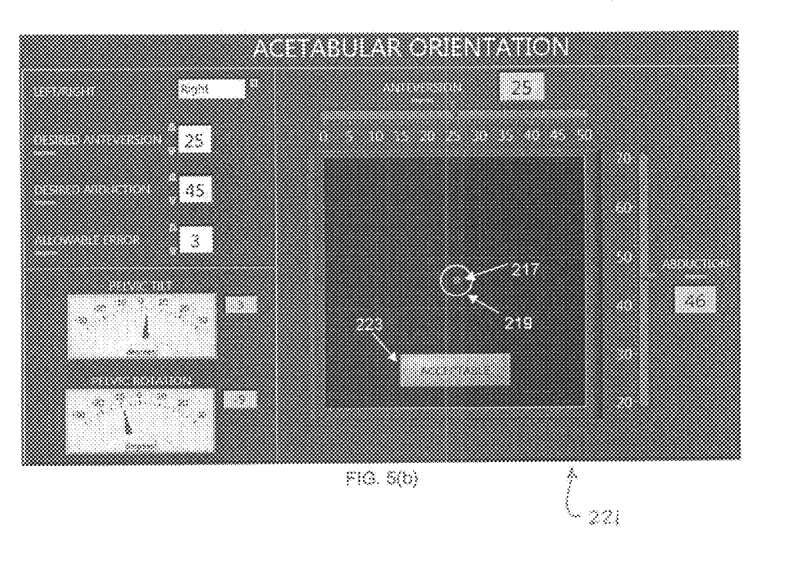

As seen most clearly in the sample screen display 221 shown in FIG. 5(b), once cursor 217 is positioned within ring 219, a corresponding signal is sent from processor 121 to inform the surgeon that the proper orientation of component 163 has been achieved. In the present example, a pop-up tab 223 displaying the word "acceptable" is provided on graph 215 to provide positive feedback. However, it is to be understood that alternative signals (e.g., an auditory alarm or flashing illumination signal) could be used in place of tab 223 without departing from the spirit of the present invention.

With component 163 properly oriented, the surgeon then permanently secures component 163 to pelvis 11. For example, the surgeon may impact component 163 within reamed acetabulum 12 by striking the distal end of inserter 161 with a mallet.

It should be noted that graphical user interface 211 could be provided with additional information to assist the surgeon during the implantation process. For example, in the present embodiment, a pelvic tilt meter 225 and a pelvic rotation meter 227 are provided on graphical user interface 211 to provide pelvic orientation information that is potentially useful to the surgeon.

It should also be noted that system 111 is not limited to providing a positive feedback signal (i.e., a signal when component 163 is properly oriented relative to pelvis 11). Rather, system 111 could be alternatively or additionally designed to provide a negative feedback signal when undesirable conditions are detected, such as retroversion of acetabular component 163.

As noted above, system 111 is not limited to use in guiding proper orientation of an acetabular component within the pelvis during implantation. Rather, it is envisioned that alternative surgical procedures could be similarly implemented using system 111 without departing from the spirit of the present invention. In particular, it is envisioned that system 111 could be used in connection with any surgical procedure that requires real-time guidance in maintaining a surgical instrument within a particular range of spatial orientation relative to at least one anatomical reference point.

For example, system 111 could be similarly used to prepare the acetabulum for the subsequent implantation of an acetabular component. As noted above, prior to implanting an acetabular component, articular cartilage and subchondral bone is removed from the acetabulum using a reaming instrument, or reamer. A traditional reamer includes an elongated longitudinal shaft on which is coaxially mounted a motor-driven, hemispherical reamer head. Accordingly, it is to be understood that by placing tool sensor 119-2 onto the longitudinal shaft of a reamer, system 111 can be used in a similar capacity to assist the surgeon in reaming the acetabulum in the proper orientation.

The embodiment shown in the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A surgical guidance system for use in properly orienting a surgical instrument relative to at least one anatomical reference point on a patient, the system comprising:
    (a) a reference sensor configured to be fixedly coupled to a support device configured to contact and retain a patient at a particular location relative to at least one anatomical reference point, the reference sensor configured to measure both gravitational and magnetic field vectors that define a first set of spatial orientation data relative to a reference coordinate system;
    (b) a tool sensor configured to be coupled to a surgical instrument, the tool sensor configured to measure both gravitational and magnetic field vectors that define a second set of spatial orientation data relative to said reference coordinate system; and
    (c) a processor in electronic communication with the reference sensor and the tool sensor, the processor configured to collect the first and second sets of spatial orientation data, the processor configured to calculate an actual orientation of the surgical instrument relative to the at least one anatomical reference point using the first and second sets of spatial orientation data.

2. The surgical guidance system as claimed in claim 1 wherein calculation of the actual orientation of the surgical instrument relative to the at least one anatomical reference point by the processor is not affected by either axial rotation or longitudinal displacement of the tool sensor relative to the surgical instrument.

3. The surgical guidance system as claimed in claim 1 wherein each sensor includes an accelerometer for measuring the gravitational vector relative to its corresponding reference axis and a magnetometer for measuring the magnetic field vector relative to its corresponding reference coordinate system.

4. The surgical guidance system as claimed in claim 1 wherein the gravitational and magnetic field vectors measured by each sensor define said fixed coordinate system which includes an X axis, a Y axis and a Z axis.

5. The surgical guidance system as claimed in claim 4 wherein the roll for each sensor is defined by the degree of rotation of the sensor relative to the X axis of the fixed coordinate system.

6. The surgical guidance system as claimed in claim 5 wherein the pitch for each sensor is defined by the degree of rotation of the sensor relative to the Y axis of the fixed coordinate system.

7. The surgical guidance system as claimed in claim 6 wherein the yaw for each sensor is defined by the degree of rotation of the sensor relative to the Z axis of the fixed coordinate system.

8. The surgical guidance system as claimed in claim 7 wherein the roll, pitch and yaw for each sensor are represented by a corresponding matrix.

9. The surgical guidance system as claimed in claim 8 wherein the processor is configured to multiply together the roll, pitch and yaw matrices for each sensor to yield a transformation matrix that identifies movement of the sensor relative to the fixed coordinate system.

10. The surgical guidance system as claimed in claim 9 wherein the processor is configured to multiply together the roll, pitch and yaw matrices for each sensor in a defined sequence.

11. The surgical guidance system as claimed in claim 10 wherein the processor is configured to designate the yaw matrix as the last matrix in the defined multiplication sequence.

12. The surgical guidance system as claimed in claim 8 wherein an angle of anteversion is represented by the pitch of the tool sensor minus the pitch of the reference sensor.

13. The surgical guidance system as claimed in claim 8 wherein an angle of abduction is represented by the roll of the tool sensor minus the roll of the reference sensor.

14. The surgical guidance system as claimed in claim 13 wherein the angle of abduction does not depend on the yaw for the tool sensor.

15. The surgical guidance system as claimed in claim 12 wherein the angle of anteversion does not depend on the yaw for the tool sensor.

* * * * *